United States Patent
O'Reilly et al.

(10) Patent No.: US 11,432,802 B2
(45) Date of Patent: Sep. 6, 2022

(54) SYSTEM AND METHOD FOR CONTROLLING FOCUSED ULTRASOUND TREATMENT

(71) Applicant: SUNNYBROOK RESEARCH INSTITUTE, Toronto (CA)

(72) Inventors: Meaghan Anne O'Reilly, Toronto (CA); Kullervo Henrik Hynynen, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 0 days.

(21) Appl. No.: 16/921,395

(22) Filed: Jul. 6, 2020

(65) Prior Publication Data
US 2020/0330075 A1 Oct. 22, 2020

Related U.S. Application Data

(62) Division of application No. 13/538,350, filed on Jun. 29, 2012, now Pat. No. 10,702,244.
(Continued)

(51) Int. Cl.
*A61B 8/08* (2006.01)
*A61N 7/02* (2006.01)
(Continued)

(52) U.S. Cl.
CPC ............ *A61B 8/481* (2013.01); *A61B 8/0808* (2013.01); *A61N 7/02* (2013.01); *A61B 8/4488* (2013.01);
(Continued)

(58) Field of Classification Search
CPC .................. A61B 8/481; A61B 8/0808; A61B 2017/00106; A61B 8/4488;
(Continued)

(56) References Cited

U.S. PATENT DOCUMENTS

| | | | |
|---|---|---|---|
| 2006/0264809 A1 | 11/2006 | Hansmann | |
| 2010/0056924 A1* | 3/2010 | Powers | A61B 8/481 600/458 |
| 2010/0113983 A1 | 5/2010 | Heckerman | |

FOREIGN PATENT DOCUMENTS

| | | |
|---|---|---|
| CN | 1847824 | 10/2006 |
| WO | 2010108104 | 9/2010 |

(Continued)

OTHER PUBLICATIONS

Cho E, et al. Two-photon fluorescence microscopy study of cerebrovascular dynamics in ultrasound-induced blood-brain barrier opening. J Cereb Blood Flow Metab 2011;31(9):1852-1862.
(Continued)

*Primary Examiner* — Bo Joseph Peng
(74) *Attorney, Agent, or Firm* — Quarles & Brady LLP

(57) ABSTRACT

A system and method for controlling the delivery of ultrasound energy to a subject is provided. In particular, such a system and method are capable of safely disrupting the blood-brain barrier. Ultrasound energy is delivered to produce cavitation of an ultrasound contrast agent at a selected pressure value. An acoustic signal is acquired following cavitation, from which a signal spectrum is produced. The signal spectrum is analyzed for the presence of harmonics, such as subharmonics or ultraharmonics. When subharmonics or ultraharmonics are present, the pressure value is decreased for subsequent sonications. If a previous sonication resulted in no subharmonics or ultraharmonics being generated, then the pressure value may be increased. In this manner, the blood-brain barrier can be advantageously disrupted while mitigating potentially injurious effects of the sonication.

4 Claims, 3 Drawing Sheets

Related U.S. Application Data

(60) Provisional application No. 61/502,559, filed on Jun. 29, 2011.

(51) Int. Cl.
*A61N 7/00* (2006.01)
*A61B 17/00* (2006.01)
*A61B 8/00* (2006.01)
*A61B 90/00* (2016.01)

(52) U.S. Cl.
CPC ............... *A61B 2017/00106* (2013.01); *A61B 2090/374* (2016.02); *A61N 2007/0091* (2013.01); *A61N 2007/0095* (2013.01)

(58) Field of Classification Search
CPC ................ A61B 2090/374; A61N 7/02; A61N 2007/0095; A61N 2007/0091
See application file for complete search history.

(56) References Cited

FOREIGN PATENT DOCUMENTS

| | | |
|---|---|---|
| WO | 2011027264 | 3/2011 |
| WO | 2011035312 | 3/2011 |
| WO | 2012162664 | 11/2012 |

OTHER PUBLICATIONS

Choi JJ, et al. Molecules of various pharmacologically-relevant sizes can cross the ultrasound-induced blood-brain barrier opening in vivo. Ultrasound Med Biol 2010;36(1):58-67.

Choi, et al., "Microbubble-Size Dependence of Focused Ultrasound-Induced Blood-Brain Barrier Opening in Mice In Vivo," IEEE Trans. Biomed. Eng., 2010; 57:145-154.

Chopra, et al., "Influence of Exposure Time and Pressure Amplitude on Blood-Brain-Barrier Opening using Transcranial Ultrasound Exposures," ACS Chem. Neurosci., 2010; 1:391-398.

Chopra, Rajiv, et al. "An MRI-compatible system for focused ultrasound experiments in small animal models." Medical physics 36.5 (2009): 1867-1874.

European Patent Office Search Report for application 12804850.1, 6 pages, dated May 21, 2015.

Hynynen K, et al. Noninvasive MR imaging-guided focal opening of the blood-brain barrier in rabbits. Radiology 2001;220(3):640-646.

International Search Report and Written Opinion for application PCS/CA2012/050445, 9 pages, dated Oct. 29, 2012.

Jordao, et al., "Antibodies Targeted to the Brain with Image-Guided Focused Ultrasound Reduces Amyloid-Beta Plaque Load in the TgCRND8 Mouse Model of Alzheimer's Disease," PLoS One 2010;5:e10549.

Kinoshita, et al., "Noninvasive Localized Delivery of Herceptin to the Mouse Brain by MRI-Guided Focused Ultrasound-Induced Blood-Brain Barrier Disruption," Proc. Natl. Acad Sci. USA, 2006; 103:11719-11723.

McDannold, et al., "Effects of Acoustic Parameters and Ultrasound Contrast Agent Dose on Focused-Ultrasound Induced Blood-Brain Barrier Disruption," Ultrasound Med. Biol., 2008; 34:930-937.

McDannold, et al., "Targeted Disruption of the Blood-Brain Barrier with Focused Ultrasound: Association with Cavitation Activity," Phys. Med. Biol., 2006; 51:793-807.

Neppiras EA. Acoustic cavitation. Phys Rep 1980;61(3):159-251.

O'Reilly et al. "A PVDF Receiver for Ultrasound Monitoring of Transcranial Focused Ultrasound Therapy," IEEE Transactions on Biomedical Engineering, 2010; 57(9):2286-2294.

O'Reilly, et al., "The Impact of Standing Wave Effects on Transcranial Focused Ultrasound Disruption of the Blood-Brain Barrier in a Rat Model," Phys. Med. Biol., 2010; 55:5251-5267.

Pardridge WM. The blood-brain barrier: bottleneck in brain drug development. NeuroRx 2005;2(1):3-14.

Sijl, Jeroen, et al. "Subharmonic behavior of phospholipid-coated ultrasound contrast agent microbubbles." The Journal of the Acoustical Society of America 128.5 (2010): 3239-3252.

Tung, et al., "In Vivo Transcranial Cavitation Threshold Detection During Ultrasound-Induced Blood-Brain Barrier Opening in Mice," Phys Med. Biol., 2010; 55:6141-6155.

Yang FY, et al. Effect of ultrasound contrast agent dose on the duration of focused-ultrasound-induced blood-brain barrier disruption. J Acoust Soc Am 2009;126(6):3344-3349.

Yang, et al., Quantitative Evaluation of the Use of Microbubbles with Transcranial Focused Ultrasound on Blood-Brain-Barrier Disruption, Ultrason. Sonochem., 2008; 15:636-643.

\* cited by examiner

SYSTEM AND METHOD FOR CONTROLLING FOCUSED ULTRASOUND TREATMENT

CROSS-REFERENCE TO RELATED APPLICATIONS

This application is a divisional of U.S. Utility patent application Ser. No. 13/538,350 filed Jun. 29, 2012, which issued on Jul. 7, 2020 as U.S. Pat. No. 10,702,244, which claims the benefit of U.S. Provisional Patent Application 61/502,559, filed Jun. 29, 2011, which are incorporated by reference herein in their entirety for all purposes.

STATEMENT REGARDING FEDERALLY SPONSORED RESEARCH

This invention was made with government support under EB003268 and EB000705 awarded by the National Institutes of Health. The government has certain rights in the invention.

BACKGROUND OF THE INVENTION

The field of the invention is systems and methods for focused ultrasound. More particularly, the invention relates to systems and methods for controlling the delivery of focused ultrasound.

Focused ultrasound ("FUS") disruption of the blood-brain barrier ("BBB") using circulating microbubbles is a field of increasing research with the potential to revolutionize treatment of brain and central nervous system ("CNS") disorders. The BBB prevents passage of molecules from the vasculature into the brain tissue when the molecules are larger than around five hundred Daltons, thereby significantly reducing the efficacy of pharmaceutical and other agents.

FUS disruption of the BBB has been successfully used to deliver amyloid-beta antibodies, as described by J. F. Jordao, et al., in "Antibodies Targeted to the Brain with Image-Guided Focused Ultrasound Reduces Amyloid-Beta Plaque Load in the TgCRND8 Mouse Model of Alzheimer's Disease," PLoS One 2010; 5:e10549; large molecule chemotherapy agents, as described by M. Kinoshita, et al., in "Noninvasive Localized Delivery of Herceptin to the Mouse Brain by MRI-Guided Focused Ultrasound-Induced Blood-Brain Barrier Disruption," Proc. Natl. Acad. Sci. USA, 2006; 103:11719-11723; and other large molecules of clinically relevant size, as described by J. J. Choi, et al., in "Molecules of Various Pharmacologically-Relevant Sizes Can Cross the Ultrasound-Induced Blood-Brain Barrier Opening In Vivo," Ultrasound Med. Biol., 2010; 36:58-67.

Currently, the greatest limitation for the clinical translation of FUS BBB disruption ("BBBD") is the lack of a real-time technique for monitoring the delivery of FUS to the subject. Disruption can be evaluated using contrast-enhanced magnetic resonance imaging ("MRI"), but such methods provide insufficient temporal resolution to provide real-time feedback.

The introduction of ultrasound contrast agents, such as microbubble contrast agents, to the brain can be seen as a safety concern, especially when using transcranial FUS. Moreover, the use of ultrasound in the skull cavity has been known to make estimation of in situ pressure magnitudes and distributions more difficult, as described by M. A. O'Reilly, et al., in "The Impact of Standing Wave Effects on Transcranial Focused Ultrasound Disruption of the Blood-Brain Barrier in a Rat Model," Phys. Med. Biol., 2010; 55:5251-5267. This increased difficulty in pressure estimation when using transcranial ultrasound highlights the need for a real-time technique to monitor the microbubble behavior during FUS induced BBBD.

Studies have been conducted to examine the effects of various acoustic and contrast agent parameters on BBBD in an attempt to identify optimal disruption parameters. For example, see the studies described by F.-Y. Yang, et al., in Quantitative Evaluation of the Use of Microbubbles with Transcranial Focused Ultrasound on Blood-Brain-Barrier Disruption," Ultrason. Sonochem., 2008; 15:636-643; by N. McDannold, et al., in "Effects of Acoustic Parameters and Ultrasound Contrast Agent Dose on Focused-Ultrasound Induced Blood-Brain Barrier Disruption," Ultrasound Med. Biol., 2008; 34:930-937; by R. Chopra, et al., in "Influence of Exposure Time and Pressure Amplitude on Blood-Brain-Barrier Opening using Transcranial Ultrasound Exposures," ACS Chem. Neurosci., 2010; 1:391-398; and by J. J. Choi, et al., in "Microbubble-Size Dependence of Focused Ultrasound-Induced Blood-Brain Barrier Opening in Mice In Vivo," IEEE Trans. Biomed. Eng., 2010; 57:145-154.

Other studies have preferred to examine the microbubble emissions during BBBD in order to identify an emissions characteristic that could identify an appropriate treatment endpoint. For example, a sharp increase in harmonic emissions during sonications resulting in successful BBBD has been observed, as described by N. McDannold, et al., in "Targeted Disruption of the Blood-Brain Barrier with Focused Ultrasound: Association with Cavitation Activity," Phys. Med. Biol., 2006; 51:793-807. In another study, the presence of the fourth and fifth harmonics where observed when BBBD occurred, as described by Y.-S. Tung, et al., in "In Vivo Transcranial Cavitation Threshold Detection During Ultrasound-Induced Blood-Brain Barrier Opening in Mice," Phys. Med. Biol., 2010; 55:6141-6155. It was observed that these higher harmonics were absent when BBBD was unsuccessful; however, harmonic signal content can arise from the tissue or coupling media, and not just the circulating microbubbles. As a result, these harmonic signal components may not result in the most robust method of controlling treatments.

It would therefore be desirable to provide a system and method for controlling the delivery of ultrasound energy to a subject such that blood-brain barrier disruption can be achieved without injury to the subject.

SUMMARY OF THE INVENTION

A system and method for controlling the delivery of ultrasound energy to a subject is provided. In particular, such a system and method are capable of safely disrupting the blood-brain barrier. Ultrasound energy is delivered to produce cavitation of an ultrasound contrast agent at a selected pressure value. An acoustic signal is acquired following cavitation, from which a signal spectrum is produced. The signal spectrum is analyzed for the presence of harmonics, such as subharmonics or ultraharmonics. When subharmonics or ultraharmonics are present, the pressure value is decreased for subsequent sonications. If a previous sonication resulted in no subharmonics or ultraharmonics being generated, then the pressure value may be increased. In this manner, the blood-brain barrier can be advantageously disrupted while mitigating potentially injurious effects of the sonication.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A system and method for controlling the delivery of ultrasound energy to a subject with a focused ultrasound ("FUS") system is provided. Particularly, ultrasound energy is delivered to the subject in a controlled manner such that blood-brain barrier disruption can be achieved without injury to the subject. The presence of subharmonics or ultraharmonics in the spectral profile of acoustic signals acquired following the delivery of ultrasound energy to the subject is utilized to adjust parameters of subsequent sonications, such as acoustic pressure. Preferably, microbubble contrast agents are used and the emissions from these microbubbles during sonication are spectrally analyzed in real-time to guide subsequent sonications. The provided system and method may also be utilized to perform acoustically controlled non-thermal lesioning using circulating microbubbles for treating tumors in near-skull regions where thermal ablation is unachievable. Since the blood-brain barrier is also disrupted in the focal region during treatment, a therapy agent can also be delivered after initial lesioning in order to improve treatment efficacy.

Figure 1:
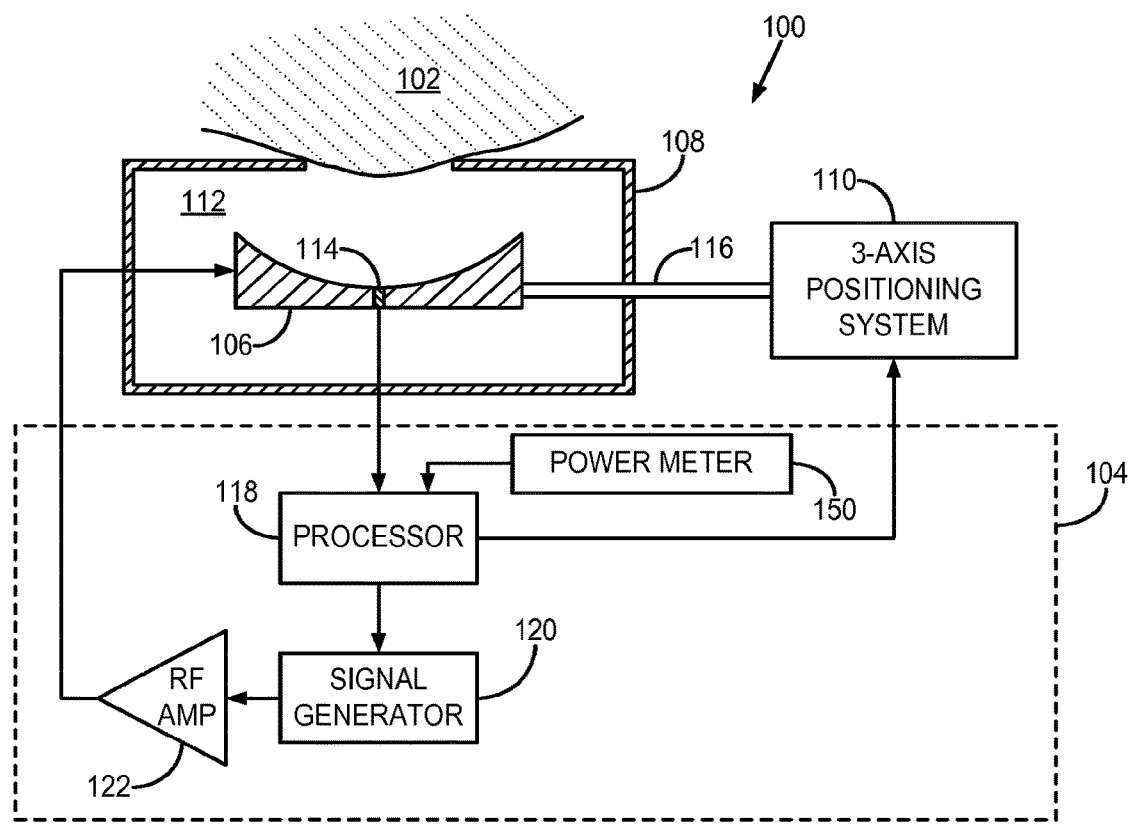
FIG. 1 is a block diagram of an exemplary focused ultrasound ("FUS") system that can be employed when practicing some embodiments of the present invention.

Referring to FIG. 1, an exemplary focused ultrasound ("FUS") system 100 for delivering focused ultrasound to a subject 102 is illustrated. The FUS system includes a controller 104, an ultrasound transducer 106, an enclosure 108, and a positioning system 110. The enclosure 108 houses the ultrasound transducer 106 and provides an interface with the subject 102 such that ultrasound energy can be efficiently transferred from the ultrasound transducer 106 to the subject 102. By way of example, the enclosure 108 is filled with an acoustic coupling medium 112, which allows for a more efficient propagation of ultrasound energy than through air. Exemplary acoustic coupling media 112 include water, such as degassed water. Advantageously, the ultrasound transducer 106 includes a signal detector 114, such as a hydrophone. By way of example, the signal detector 114 may include a wideband polyvinylidene fluoride ("PVDF") hydrophone, such as those described by M. A. O'Reilly and K. Hynynen in "A PVDF Receiver for Ultrasound Monitoring of Transcranial Focused Ultrasound Therapy," IEEE Transactions on Biomedical Engineering, 2010; 57(9):2286-2294. The ultrasound transducer 106 is coupled to the positioning system 110 by way of a support 116. The positioning system 110 is advantageously a three-axis positioning system that provides precise and accurate positioning of the ultrasound transducer 106 in three dimensions.

The controller 104 generally includes a processor 118, a signal generator 120, and a radio frequency ("RF") amplifier 122. The signal generator 120 may include, for example, a function generator, and is configured to provide a driving signal that directs the ultrasound transducer 106 to generate ultrasound energy. The driving signal produced by the signal generator 120 is amplified by the RF amplifier 122 before being received by the ultrasound transducer 106. The ultrasound transducer 106 may also be a phased array transducer. When the FUS system 100 is used during a magnetic resonance guided FUS ("MRgFUS") application, the controller 104 can be positioned inside or outside of the magnet room of the magnetic resonance imaging ("MRI") system.

The processor 118 is in communication with the signal generator 120 and directs the signal generator 120 to produce the driving signal that is delivered to the ultrasound transducer 106. As will be described below in detail, the processor 118 may be configured to adjust properties of the driving signal such that the ultrasound energy pressure produced by the ultrasound transducer 106 is adjusted in accordance with embodiments of the present invention. For example, the processor 118 may be configured to use information related to whether harmonics were identified in a signal spectrum, as described below, to adjust at least one of a frequency, a burst length, a pulse repetition frequency, a sonication start time, a sonication end time, and a sonication duration.

The processor 118 receives acoustic signals from the signal detector 114. As will be described below in detail, the feedback information provided by the signal detector 114 is utilized by the processor 118 to direct the appropriate adjustments in ultrasound energy. The processor 118 is also in communication with the positioning system 110, and is configured to direct the positioning system 110 to move the position of the ultrasound transducer 106 during a sonication procedure. In the case that the ultrasound transducer 106 is a phased array transducer, the controller 104 may adjust the phase and/or amplitude of the driving RF signal to each transducer element to control the location of the focal spot. The processor 118 may also be in communication with a power meter 150. In this configuration, the processor is configured to receive reflected electrical power data from the power meter and to analyze the reflected electrical power data to determine whether an ultrasound contrast agent is circulating through a volume-of-interest in the subject.

The ultrasound transducer 106 is preferably a spherically-focused transducer matched to a desired frequency using an external matching circuit. In some configurations, the ultrasound transducer 106 is designed so that the signal detector 114 may be mounted in the center of the ultrasound transducer 106.

Figure 2:
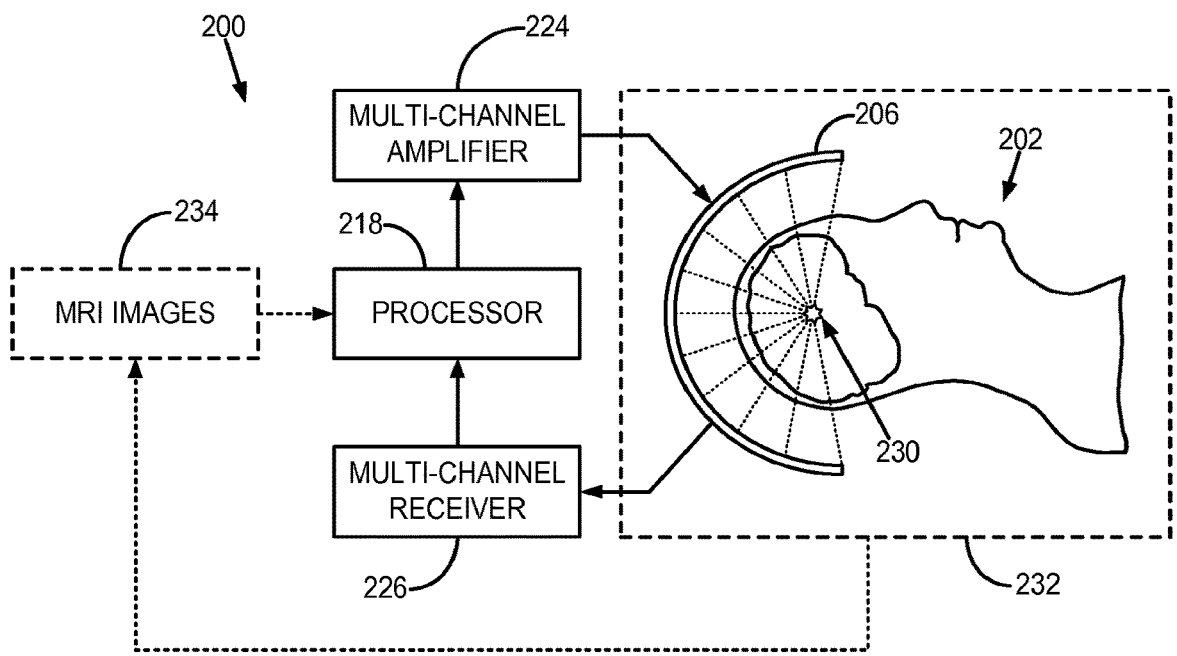
FIG. 2 is a block diagram of another exemplary FUS system that can be employed when practicing some embodiments of the present invention.

Referring now to FIG. 2, in some instances, an FUS system 200 may be configured more particularly for transcranial ultrasound applications in human subjects. In such a system, a subject 202 receives ultrasound energy from a transducer 206 that is configured to surround an extent of the subject's head. For example, the transducer 206 may be a hemispherical array of transducer elements. The FUS system 200 may include a cooling system, such as a sealed water system with an active cooling and degassing capacity, so that an appropriate and comfortable temperature of the skull and skin of the subject 202 may be maintained during treatment.

The FUS system 200 includes a processor 218 that is in communication with a multi-channel amplifier 224 and a multi-channel receiver 226. The multi-channel amplifier 224 received driving signals from the processor 218 and, in turn, directs the transducer elements of the transducer 206 to generate ultrasound energy. The multi-channel receiver 226 receives acoustic signals during sonications and relays these signals to the processor 218 for processing in accordance with embodiments of the present invention. The processor 218 may also be configured to adjust the driving signals in response to the acoustic signals received by the multi-channel receiver 226. For example, the phase and/or amplitude of the driving signals may be adjusted so that ultrasound energy is more efficiently transmitted through the skull of the subject 202 and into the target volume-of-interest 230. Furthermore, the acoustic signals may also be analyzed to determine whether and how the extent of the focal region should be adjusted. As will be described below in detail, magnetic resonance imaging ("MRI") may also be used to guide the application of ultrasound energy to the subject 202. Thus, an MRI system, generally indicated as dashed box 232, may be used to acquired MRI images 234 of the subject 202. The MRI images 234 may then be provided to the processor 218 to adjust the parameters of the sonications. For example, the phase and/or amplitude of the driving signals may be adjusted so that ultrasound energy is more efficiently transmitted through the skull of the subject 202 and into the target volume-of-interest 230. It is noted that other imaging modalities, such as computed tomography ("CT"), positron emission tomography ("PET"), single-photon emission computed tomography ("SPECT"), and ultrasound may also be used to guide the treatment.

Figure 3:
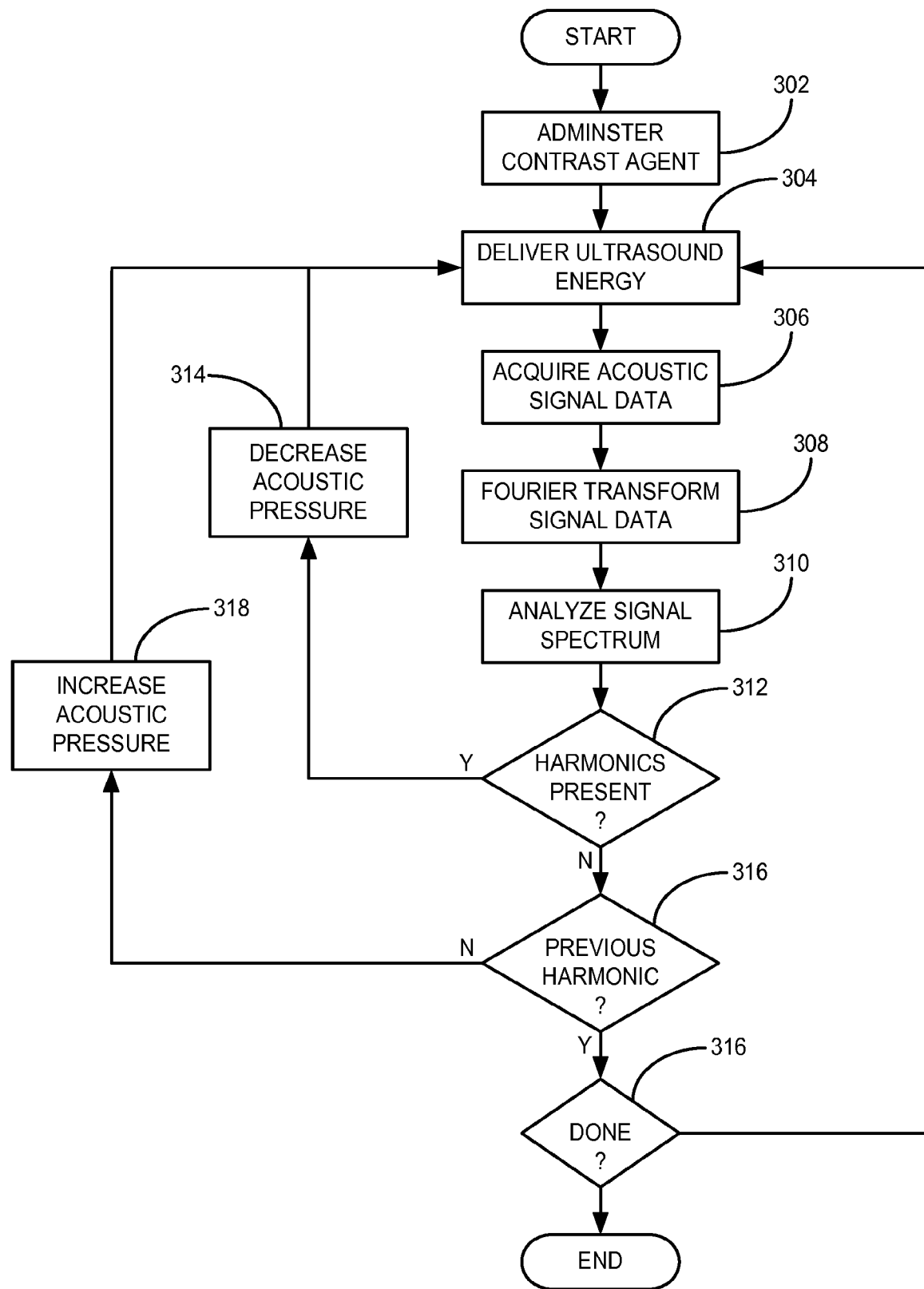
FIG. 3 is a flowchart setting forth the steps of an exemplary method for controlling sonications produced by an FUS system such that blood-brain barrier disruption can be achieved without injury to a subject.

Referring now to FIG. 3, a flowchart setting forth the steps of an exemplary method for controlling a focused ultrasound ("FUS") system is illustrated. This method for controlling an FUS system provides for the delivery of ultrasound energy to a subject so that an advantageous disruption of the blood-brain barrier is achieved without injury to the subject. First, a contrast agent is administered to the subject, as illustrated at step 302. Exemplary contrast agents include microbubble ultrasound contrast agents, such as those marketed under the name Definity® (Lantheus Medical Imaging; North Billerica, Mass.). As the contrast agent is circulating through the subject, ultrasound energy is delivered to a target volume using a focused ultrasound ("FUS") system, as indicated at step 304. The ultrasound energy is delivered with delivery parameters, such as acoustic power, that are selected so as to produce a desired pressure in the target volume. By way of example, the delivery of ultrasound energy, or "sonication," may be performed using continuous wave bursts having a fundamental frequency of 551.5 kHz. Acoustic signal data is acquired following the delivery of the ultrasound energy, as indicated at step 306. This signal data is then processed to determine whether the ultrasound energy delivered in the next delivery should be adjusted.

The acquired acoustic signal is first transformed into frequency space to produce a signal spectrum, as indicated at step 308. For example, a fast Fourier transform is applied to the acoustic signal to produce the signal spectrum. The produced signal spectrum is then analyzed, as indicated at step 310. By way of example, the signal spectrum is integrated over to identify the presence of harmonics in the signal spectrum. More particularly, the signal spectrum may be analyzed to identify the presence of subharmonics or ultraharmonics of the fundamental frequency, $f_0$, of the ultrasound energy, such as $0.5f_0$, $1.5f_0$, and $2.5f_0$. By integrating over the signal spectrum around the frequency values for these subharmonics or ultraharmonics, and comparing the results with the respective spectral values for a signal spectrum acquired before the contrast agent was administered to the subject, the presence of the subharmonics or ultraharmonics can be evaluated.

After analyzing the signal spectrum, a determination is made whether one or more subharmonics or ultraharmonics are present in the signal spectrum, as indicated at decision block 312. If one or more subharmonics or ultraharmonics are identified in the signal spectrum, then the pressure of the ultrasound energy is decreased before the next delivery, as indicated at step 314. For example, the pressure may be decreased in accordance with:

$$P_{i+1} = \gamma \cdot P_i \quad (1);$$

where $P_i$ is the pressure used for the $i^{th}$ sonication, $P_{i+1}$ is the pressure that will be used for the $(i+1)^{th}$ sonication, and $\gamma$ is a factor that decreases the pressure to a target level as a normalized value of pressure for subharmonic or ultraharmonic emissions. An exemplary target level of ultrasound energy pressure includes a user selected percentage of the pressure required to induce detectable levels of subharmonic or ultraharmonic emissions.

After this adjustment, the next ultrasound delivery is performed, and steps 304-312 may be repeated if more ultrasound energy is to be delivered to the subject. If no subharmonics or ultraharmonics are present in the signal spectrum then a determination is made at decision block 316 whether subharmonics or ultraharmonics were present in signal spectra from previous ultrasound energy deliveries. For example, if the first sonication results in a signal spectrum with no ultraharmonics, then this information is stored and, following the second sonication, the determination at decision block 316 would be that no ultraharmonics were present in the previous signal spectrum. If no ultraharmonics were identified in the previous signal spectrum, then it may be appropriate to increase the ultrasound energy pressure for the next sonication. Thus, as indicated at step 318, the pressure can be increased. For example, the pressure may be increased in accordance with:

$$P_{i+1} = P_i + \delta P \quad (2);$$

where $\delta P$ is an incremental pressure value. If subharmonics or ultraharmonics were identified in the previous signal spectrum, then the pressure is maintained at its current level, or reduced depending on the level of tissue damage that is desired. If blood-brain barrier disruption is desired without other effects on tissue, then the pressure level may be reduced for the subsequent sonications. If more sonications are desired, then the process loops back to perform steps 304-318, as indicated at decision block 320.

Thus, a system and method for actively controlling blood-brain barrier disruption using acoustic emissions monitoring has been provided. Using the provided system and method, it is contemplated that the blood-brain barrier can be safely disrupted without knowledge of in situ pressures.

Figure 4:
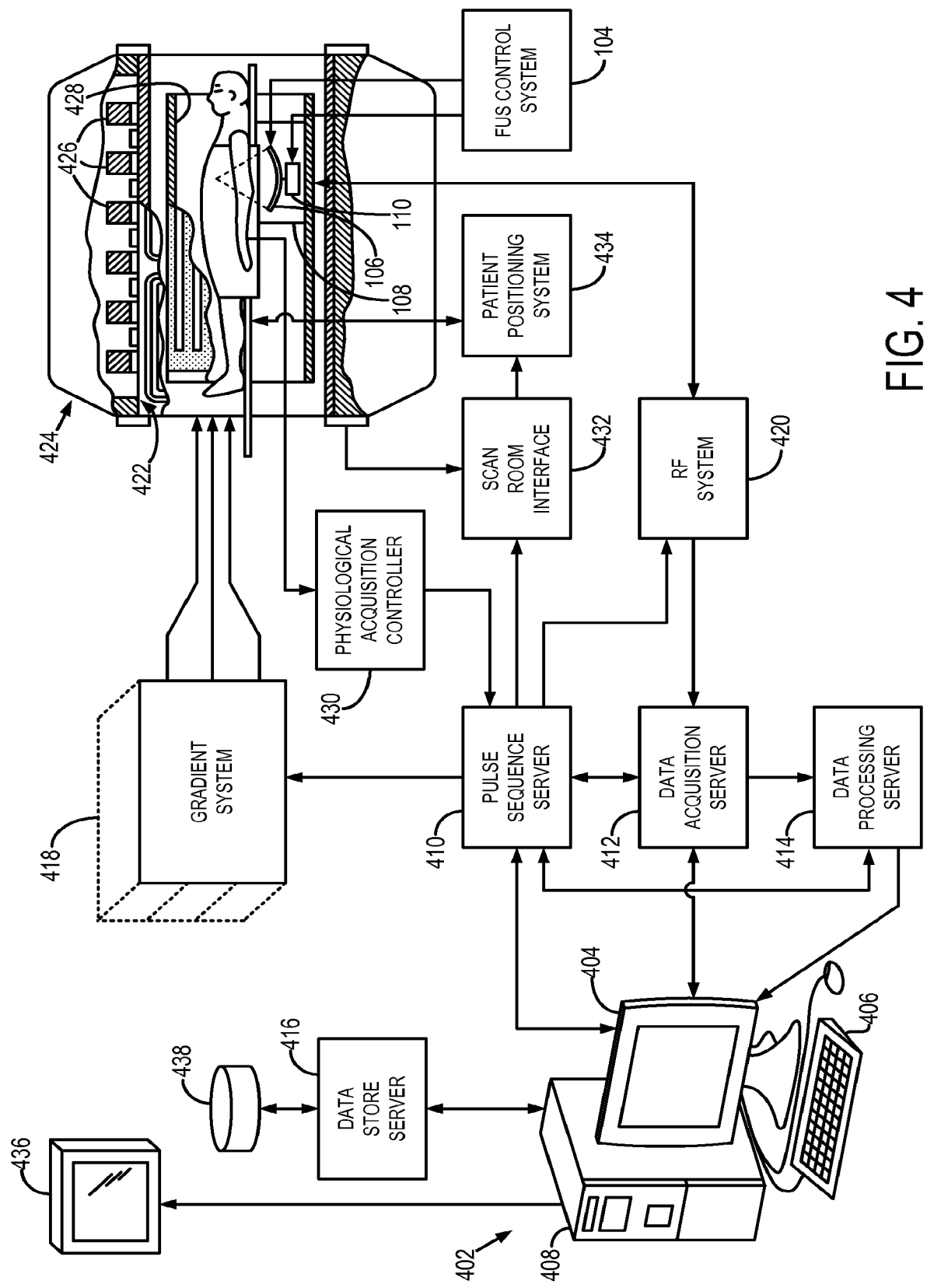
FIG. 4 is a block diagram of an exemplary magnetic resonance guided focused ultrasound ("MRgFUS") system that is employed when practicing some embodiments of the present invention.

The aforementioned FUS treatment can be further monitored and guided with the aid of magnetic resonance imaging ("MRI"). To this end, a magnetic resonance guided focused ultrasound ("MRgFUS") system may be utilized. Referring particularly now to FIG. 4, an exemplary MRgFUS system 400 is illustrated. The MRgFUS system 400 includes a workstation 402 having a display 404 and a keyboard 406. The workstation 402 includes a processor 408, such as a commercially available programmable machine running a commercially available operating system. The workstation 402 provides the operator interface that enables scan prescriptions to be entered into the MRgFUS system 400. The workstation 402 is coupled to four servers: a pulse sequence server 410; a data acquisition server 412; a data processing server 414, and a data store server 416. The workstation 402 and each server 410, 412, 414 and 416 are connected to communicate with each other.

The pulse sequence server 410 functions in response to instructions downloaded from the workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding MR signals. The gradient coil assembly 422 forms part of a magnet assembly 424 that includes a polarizing magnet 426 and a whole-body RF coil 428.

RF excitation waveforms are applied to the RF coil 428, or a separate local coil (not shown in FIG. 4), by the RF system 420 to perform the prescribed magnetic resonance pulse sequence. Responsive MR signals detected by the RF coil 428, or a separate local coil (not shown in FIG. 4), are received by the RF system 420, amplified, demodulated, filtered, and digitized under direction of commands produced by the pulse sequence server 410. The RF system 420 includes an RF transmitter for producing a wide variety of RF pulses used in MR pulse sequences. The RF transmitter is responsive to the scan prescription and direction from the pulse sequence server 410 to produce RF pulses of the desired frequency, phase, and pulse amplitude waveform. The generated RF pulses may be applied to the whole body RF coil 428 or to one or more local coils or coil arrays (not shown in FIG. 4).

The RF system 420 also includes one or more RF receiver channels. Each RF receiver channel includes an RF amplifier that amplifies the MR signal received by the coil 428 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad (3);$$

and the phase of the received MR signal may also be determined:

$$\varphi = \tan^{-1}\left(\frac{Q}{I}\right). \quad (4)$$

The pulse sequence server 410 also optionally receives patient data from a physiological acquisition controller 430. The controller 430 receives signals from a number of different sensors connected to the patient, such as electrocardiograph ("ECG") signals from electrodes, or respiratory signals from a bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized MR signal samples produced by the RF system 420 are received by the data acquisition server 412. The data acquisition server 412 operates in response to instructions downloaded from the workstation 402 to receive the real-time MR data and provide buffer storage, such that no data is lost by data overrun. In some scans, the data acquisition server 412 does little more than pass the acquired MR data to the data processor server 414. However, in scans that require information derived from acquired MR data to control the further performance of the scan, the data acquisition server 412 is programmed to produce such information and convey it to the pulse sequence server 410. For example, the data acquisition server 412 may acquire MR data and processes it in real-time to produce information that may be used to control the acquisition of MR data, or to control the sonications produced by the FUS system.

The data processing server 414 receives MR data from the data acquisition server 412 and processes it in accordance with instructions downloaded from the workstation 402. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 414 are conveyed back to the workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the workstation 402. The workstation 402 may be used by an operator to archive the images, produce films, or send the images via a network to other facilities.

The MRgFUS system may include a patient table with an integrated ultrasound transducer 106. Such an ultrasound transducer 106 is operable to perform the herein described method for providing a non-injurious disruption of the blood-brain barrier. Similar to the previously described FUS system, the ultrasound transducer 106 may be housed in an enclosure 108 that is filled with an acoustically conductive fluid, such as degassed water or a similar acoustically transmitting fluid. The ultrasound transducer 106 is preferably connected to a positioning system 110 that moves the transducer 106 within the enclosure 108, and consequently mechanically adjusts the focal zone of the transducer 106. For example, the positioning system 110 may be configured to move the transducer 106 within the enclosure 108 in any one of three orthogonal directions, and to pivot the transducer 106 about a fixed point within the enclosure 108 to change the angle of the transducer 106 with respect to a horizontal plane. When the angle of the transducer 106 is altered, the focal distance of the focal zone may be controlled electronically by changing the phase and/or amplitude of the drive signals provided to the transducer 106. These drive signals are provided to the ultrasound transducer by an FUS control system 104 that includes drive circuitry in communication with the ultrasound transducer 106 and a controller that is in communication with the positioning system 110 and drive circuitry.

The top of the enclosure 108 may include a flexible membrane that is substantially transparent to ultrasound, such as a Mylar, polyvinyl chloride ("PVC"), or other plastic materials. In addition, a fluid-filled bag (not shown) that can conform easily to the contours of a patient placed on the table may also be provided along the top of the patient table.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for controlling delivery of ultrasound energy to a subject with a focused ultrasound (FUS) system, the steps of the method comprising:
   a) administering an ultrasound contrast agent to a subject;
   b) selecting a pressure value;
   c) delivering ultrasound energy with a FUS system to a subject to produce cavitation of the contrast agent at the selected pressure;
   d) receiving an acoustic signal from the cavitation produced in step c);
   e) producing a signal spectrum from the acoustic signal received in step d);
   f) analyzing the signal spectrum produced in step d) to identify whether at least one of subharmonics and ultraharmonics is present in the signal spectrum; and
   g) updating the selected pressure value according to a weighting factor that decreases the pressure value to a target level as a normalized value of pressure for the at least one of subharmonics and ultraharmonics by using information related to whether at least one of subharmonics and ultraharmonics is present in the signal spectrum, the information being derived from the analyzed signal spectrum.

2. The method as recited in claim 1 in which step g) includes decreasing the selected pressure value when at least one of subharmonics and ultraharmonics is present in the signal spectrum.

3. The method as recited in claim 1 in which steps c)-g) are repeated for a selected period of time.

4. The method as recited in claim 3 in which step g) includes increasing the selected pressure value when, in a previous repetition of step d), at least one of subharmonics and ultraharmonics was not present in the signal spectrum.

* * * * *

UNITED STATES PATENT AND TRADEMARK OFFICE
CERTIFICATE OF CORRECTION

PATENT NO. : 11,432,802 B2
APPLICATION NO. : 16/921395
DATED : September 6, 2022
INVENTOR(S) : Meaghan Anne O'Reilly et al.

Page 1 of 1

It is certified that error appears in the above-identified patent and that said Letters Patent is hereby corrected as shown below:

In the Claims

Claim 1, Line 10, Column 10, "information related to whether at least one of" should be --information related to whether the at least one of--.

Signed and Sealed this
Twenty-fourth Day of January, 2023

Katherine Kelly Vidal
*Director of the United States Patent and Trademark Office*